(12) United States Patent
Siklosi et al.

(10) Patent No.: US 6,759,006 B1
(45) Date of Patent: Jul. 6, 2004

(54) FABRIC SANITIZATION PROCESS

(75) Inventors: Michael Peter Siklosi, Cincinnati, OH (US); James Peyton Hutchins, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/673,602

(22) PCT Filed: Apr. 16, 1999

(86) PCT No.: PCT/IB99/00688

§ 371 (c)(1),
(2), (4) Date: Oct. 18, 2000

(87) PCT Pub. No.: WO99/55390

PCT Pub. Date: Nov. 4, 1999

Related U.S. Application Data
(60) Provisional application No. 60/082,907, filed on Apr. 24, 1998.

(51) Int. Cl.[7] .................................................. A61L 2/00
(52) U.S. Cl. .............................. 422/28; 422/1; 422/5; 422/29; 422/32; 422/292; 422/294; 442/59; 510/297
(58) Field of Search ...................... 422/1, 5, 29, 28, 422/32, 292, 294; 442/59; 510/297

(56) References Cited

U.S. PATENT DOCUMENTS

| | | | |
|---|---|---|---|
| 4,336,024 A | 6/1982 | Denissenko et al. | 8/142 |
| 4,630,312 A | 12/1986 | Milstein | 383/86 |
| 4,943,392 A | 7/1990 | Hastedt et al. | 252/539 |
| 5,009,747 A | 4/1991 | Viazmensky et al. | 162/115 |
| 5,062,973 A | 11/1991 | Kellett | 252/8.75 |
| 5,066,413 A | 11/1991 | Kellett | 252/8.75 |
| 5,080,822 A | 1/1992 | VanEenam | 252/170 |
| 5,173,200 A | 12/1992 | Kellett | 252/8.8 |
| 5,238,587 A | 8/1993 | Smith et al. | 252/8.6 |
| 5,292,581 A | 3/1994 | Viazmensky et al. | 428/288 |
| 5,403,505 A | 4/1995 | Hachmann et al. | 252/106 |
| 5,492,540 A | 2/1996 | Leifheit et al. | 8/111 |
| 5,547,476 A | 8/1996 | Siklosi et al. | 8/142 |
| 5,591,236 A | 1/1997 | Roetker | 8/137 |
| 5,630,847 A | 5/1997 | Roetker | 8/137 |
| 5,630,848 A | 5/1997 | Young et al. | 8/137 |
| 5,632,780 A | 5/1997 | Siklosi | 8/137 |
| 5,658,651 A | 8/1997 | Smith et al. | 442/59 |
| 5,681,355 A | 10/1997 | Davis et al. | 8/137 |
| 5,687,591 A | 11/1997 | Siklosi et al. | 68/212 |
| 5,762,648 A | 6/1998 | Yeazell | 8/137 |
| 5,789,368 A | 8/1998 | You et al. | 510/297 |
| 5,942,484 A | 8/1999 | Roetker et al. | 510/426 |

FOREIGN PATENT DOCUMENTS

| | | | |
|---|---|---|---|
| EP | 0 429 172 A1 | 10/1990 | D06F/43/00 |
| WO | WO 97/32004 | 9/1997 | C11D/17/04 |
| WO | WO 99/16955 | 4/1999 | D06L/1/04 |

*Primary Examiner*—Krisanne Thornton
(74) *Attorney, Agent, or Firm*—Mark A. Charles; S. Robert Chuey; C. Brant Cook (57) ABSTRACT

A process for sanitizing a fabric article which is contaminated with one or more microbials. The process steps include: (a) placing the fabric article in a vapor venting bag together with a cleaning/refreshing composition comprising water; and (b) subjecting the vapor venting bag to a heat source which supplies sufficient heat to vaporize the water, thereby exposing the microbials to the resulting water vapor. This process results in at least about 50% of the microbials being killed. The cleaning/refreshing composition preferably comprises at least one antimicrobial agent selected from the group consisting of 5-chloro-2-(2,4-dichlorophenoxy)phenol, trichlorocarbanalide, hydrogen peroxide, other oxygen bleaches, 4-chloro-3,5-dimethylphenol, iodine/iodophors, chlorhexidine, phenols, phospholipids, thymol, eugeniol, geraniol, oil of lemon grass, limonene and mixtures thereof. The process of this invention preferably further comprises the step pre-treating at least a portion of the fabric with a pre-treating composition comprising an antimicrobial agent selected from the group consisting of 5-chloro-2-(2,4-dichlorophenoxy) phenol, trichlorocarbanalide, hexachlorophene, chlorhexidine, o-phenylphenol, benzylquaternium salts and mixtures thereof

20 Claims, 3 Drawing Sheets

FABRIC SANITIZATION PROCESS

This application claims the benefit of Provisional application Ser. No. 60/082,907, filed Apr. 24, 1998.

FIELD OF THE INVENTION

This invention relates to sanitization processes for use on fabrics or other solid objects.

BACKGROUND OF THE INVENTION

The sanitization of small solid objects such as eating utensils, infant toys and paraphernalia, personal grooming items such as combs and hair brushes, and the like, against bacteria can be effected by applying various antiseptic chemicals thereto. However, such chemicals may not be useful against fungi. In any event, the sanitization of larger objects such as garments by the direct application of antiseptic chemicals is expensive and inconvenient. The present invention provides an effective sanitization process which can be used in the home and is especially useful for treating fabrics in a non-immersion process. Specifically, a treatment process for sanitizing fabrics at home is disclosed.

Together with the soil and stain removal aspects of a typical dry fabric treatment process, there is also a consumer need for what can be termed fabric sanitization and "refreshment". Thus, garments which have lint, hair or other solid debris clinging to their surfaces, which may have adsorbed malodors, or which have become wrinkled or otherwise lost their fresh appearance, are often subjected to conventional commercial dry cleaning processes mainly to reestablish their freshness aspect. Such processes can also help sanitize the garments by removing or destroying microorganisms.

Attempts have been made to provide in-home dry cleaning systems. One type of non-immersion, in-home system for cleaning and refreshing garments comprises multiple single-use carrier sheets containing various liquid or gelled cleaning agents and a re-usable plastic containment bag. The garments are placed in the bag together with a sheet, and then tumbled with heating in a conventional clothes dryer. After the garments are cleaned and refreshed, the bag, which may retain traces of moisture, can then be stored for later re-use when the process is repeated.

It has now been discovered that, when properly constructed and operated, the process herein can kill or otherwise hinder the growth of bacteria and other microbials which may be present on solid articles such as soiled garments. Unexpectedly, when conducted in the vapor-venting manner of this invention, fungi are also killed or their growth inhibited. As an added advantage, the interior surfaces of the containment bag are also sanitized. Hence, when the bag is stored between uses the growth of "mildew" or bacteria in the bag is minimized.

BACKGROUND ART

The use of $H_2O_2$ in sterilization processes is described in U.S. Pat. No. 4,230,663, to Forstrom, et al., issued Oct. 28, 1980 and U.S. Pat. No. 4,169,124, to Forstrom, et al., issued Sep. 25, 1979 and U.S. Pat. No. 4,169,153 to Moore, et al., issued Sep. 25, 1979. WO 97/00993A1, published Jan. 9, 1997 to Weller, et al.; WO 97/00990A2, published Jan. 9, 1997 to Tyerech, et al.; GB 2,302,553A, published Jan. 22, 1997 to Telesca, et al.; GB 2,302,878A, published Feb. 5, 1997 to Weller, et al.; and GB 2,302,879A, published Feb. 5, 1997 to Sidoti, et al. all relate to in-dryer fabric cleaning. U.S. Pat. No. 4,532,722, issued to S. H. Sax, Aug.6, 1985, relates to a fabric conditioning device for use in a laundry dryer. A peracid-containing dry cleaning composition is described in U.S. Pat. No. 4,013,575, issued to H. Castrantas, et al., Mar. 22, 1977. Dry cleaning processes are disclosed in: U.S. Pat. No. 5,591,236, issued Jan. 7, 1997 to Roetker; U.S. Pat. No. 5,547,476, issued Aug.20, 1996, to Siklosi and Roetker; EP 429,172A1, published 29.05.91, Leigh, et al.; and in U.S. Pat. No. 5,238,587, issued Aug. 24, 1993, Smith, et al. Other references relating to dry cleaning compositions and processes, as well as wrinkle treatments for fabrics, include: GB 1,598,911; and U.S. Pat. Nos. 4,126,563, 3,949,137, 3,593,544, 3,647,354; 3,432,253 and 1,747,324; and German applications 2,021,561 and 2,460, 239, 0,208,989 and 4,007,362. Cleaning/pre-spotting compositions and methods are also disclosed, for example, in U.S. Pat. Nos. 5,102,573; 5,041,230; 4,909,962; 4,115,061; 4,886,615; 4,139,475; 4,849,257; 5,112,358; 4,659,496; 4,806,254; 5,213,624; 4,130,392; and 4,395,261. Sheet substrates for use in a laundry dryer are disclosed in Canadian 1,005,204. U.S. Pat. No. 3,956,556 and 4,007,300 relate to perforated sheets for fabric conditioning in a clothes dryer. U.S. Pat. No. 4,692,277 discloses the use of 1,2-octanediol in liquid cleaners. See also U.S. Pat. No. Pat. Nos. 3,591, 510; 3,737,387; 3,764,544; 3,882,038; 3,907,496; 4,097, 397; 4,102,824; 4,336,024; 4,594,362; 4,606,842; 4,758, 641; 4,797,310; 4,802,997; 4,943,392; 4,966,724; 4,983, 317; 5,004,557; 5,062,973; 5,080,822; 5,173,200; EP 0 213 500; EP 0 261 718; G.B. 1,397,475; WO91/09104; WO91/13145; WO 93/25654 and Hunt, D. G. and N. H. Morris, "PnB and DPnB Glycol Ethers", *HAPPI*, April 1989, pp. 78–82.

SUMMARY OF THE INVENTION

The present invention encompasses, a process for sanitizing a fabric article which is contaminated with one or more microbials. The process comprising the steps of:
  a) placing the fabric article in a vapor venting bag together with a cleaning composition comprising water;
  b) subjecting the vapor venting bag to a heat source which supplies sufficient heat to vaporize the water, thereby exposing the microbials to the resulting water vapor; and
whereby at least about 50% of the microbials are killed.

The cleaning/refreshing composition of the present invention preferably comprises from about 0.05% to about 3%, preferably from about 0.1% to about 2%, and more preferably from about 0.1% to about 1%, by weight of an antimicrobial agent selected from the group consisting of 5-chloro-2-(2,4-dichlorophenoxy)phenol, trichlorocarbanalide, hydrogen peroxide, other oxygen bleaches, 4-chloro-3,5-dimethylphenol, iodine/iodophors, chlorhexidine, phenols, phospholipids, thymol, eugeniol, geraniol, oil of lemon grass, limonene and mixtures thereof. The cleaning/refreshing composition preferably further comprises a second antimicrobial agent selected from the group consisting of alkyl alkoxy sulfates, linear alkyl benzene sulfonates, amine oxides, polyhydroxy fatty acid amides, ethoxylated alcohols, diamines, amides, alkyl polyglucosides, betaines, and mixtures thereof. Fully-formulated compositions will typically comprise water, non-ionic surfactant, perfume and one or more antimicrobial agents.

In a preferred mode, said composition is releasably absorbed in a carrier, especially a carrier which is in sheet form. Most preferably, said carrier comprises a fibrous, hydroentangled web.

The process according to this invention preferably additionally comprises subjecting said container to a tumbling action concurrently with the heating and vapor venting. In a convenient mode, the source of the heat and of the tumbling action is an integral appliance such as a conventional hot air clothes dryer.

The container used in the process is preferably a flexible bag. This bag is designed to be re-usable and, most preferably, is heat-resistant. As disclosed more fully hereinafter, the preferred container is a vapor-venting containment bag which has a Vapor Venting Equilibrium (VVE) rating of at least about 40, preferably at least about 60, more preferably no greater than about 90, and most preferably no greater than about 80.

In a preferred aspect of the process of this invention a pre-treating step is employed. The pre-treating step comprises applying a pre-treating composition to at least a portion of the fabric article, wherein the pre-treating composition preferably comprises comprises from about 0.05% to about 3%, preferably from about 0.1% to about 2%, and more preferably from about 0.1% to about 1%, by weight of an antimicrobial agent selected from the group consisting of 5-chloro-2-(2,4-dichlorophenoxy)phenol, trichlorcarbanilide, hexachlorophene, chlorhexadine, o-phenylphenol, benzylquaternium salts and mixtures thereof. Most preferably the pre-treating composition comprises 5-chloro-2-(2,4-dichlorophenoxy)phenol. The pre-treating step is especially effective in combating the malodorous compounds that are commonly associated with human body odor.

All percentages, ratios and proportions herein are by weight, unless otherwise specified. All documents cited are, in relevant part, incorporated herein by reference.

DETAILED DESCRIPTION OF THE INVENTION

The principles of sterilization and disinfection under various conditions are well-known and standard textbooks can be referred to for typical methods. Examples of various microorganisms, which are hereinafter collectively referred to as "microbials", include: germs, bacteria, viruses, parasites, fungi/spores and mixtures thereof. Microbials are known to be killed or rendered inactive by various agents. Often, dead microbials are classified as "cidal", while inactive microbials are classified as "static". This distinction is not important in the present context, since dead and inactive microbials are collectively referred to herein as "killed", and any agents that "kill" microbials are collectively referred to herein as "antimicrobials" or "antimicrobial agents". Microbial activity can be effected by additional factors including, but not limited to, concentration, pH, time of exposure to the antimicrobial agent, and the like.

By "bacterium" or "bacteria" herein is meant any of the procaryotic microorganisms having round, rodlike, spiral or filamentous single-celled or noncellular bodies.

By "fungus", "fungi", "fungi/spores" herein is meant any of the eucaryotic (Eumcophyta) microorganisms comprising saprophytic and parasitic lower plants that lack chlorophyll, and including molds, mildews, rusts, smuts, yeasts and the like.

By "mildew" and "mold" herein are meant the commonplace terms for any undesired fungal growth often from the families Erysiphaceae and Peronosporaceae, but not limited thereto. Mildew is a term which is often used pejoratively to collectively designate unwanted fungal growth on solid objects, including garments.

By "sanitizing" herein is meant that a substantial number of microbials on the fabric articles being treated are killed. By a "substantial number" it is meant that at least about 50%, preferably at least about 90%, more preferably at least about 95%, most preferably at least about 99%, of the microbials present on the fabric articles being treated are killed.

The present invention includes a process for killing microbials that uses a vapor venting bag and a cleaning/refreshing composition comprising water. But anitmicrobial agents can be included in the present cleaning/refreshing compositions for antimicrobial action if they do not adversely interfere with the surfactants used herein. Examples of anitmicrobial agents include 5-chloro-2-(2,4-dichlorophenoxy)phenol, trichlorocarbanalide, hydrogen peroxide, other oxygen bleaches, 4-chloro-3,5-dimethylphenol, iodine/iodophors, selected alcohols, chlorhexidine, phenols, phospholipids, thymol, eugeniol, geraniol, oil of lemon grass, limonene and mixtures thereof. Certain quaternary surfactants may also show antimicrobial action and may be included as a secondary antimicrobial agent.

Certain surfactants also demonstrate antimicrobial action. Examples of surfactants which are useful antimicrobial agents for use herein include anionic, cationic, nonionic, and amphoteric surfactants. Preferred examples are: alkyl alkoxy sulfates, including alkyl ethoxy sulfates, linear alkyl benzene sulfonates, amine oxides, polyhydroxy fatty acid amides, ethoxylated alcohols, diamines, amides, alkyl polyglucosides, betaines, and mixtures thereof. When the antimicrobial agent is a cationic surfactant it is preferred that the cationic surfactant is not a quaternary ammonium surfactant.

Cleaning Refreshing Articles

The cleaning/refreshing compositions of the present invention are preferably carried into the vapor venting bag via an absorbent carrier, which is preferably in the form of a sheet and is more preferably enrobed with a coversheet. The individual materials employed to assemble the absorbent carriers of the present invention are commercially available. The terms used herein to describe such materials have their conventional meanings. For purposes of clarity, certain terms used herein are defined in the text. The following description relates primarily to the use of the invention herein to clean, refresh and sanitize fabrics such as garments. However, it is to be appreciated that the same techniques can be used to sanitize other types of solid objects.

Figures 1, 2, 3, 4:
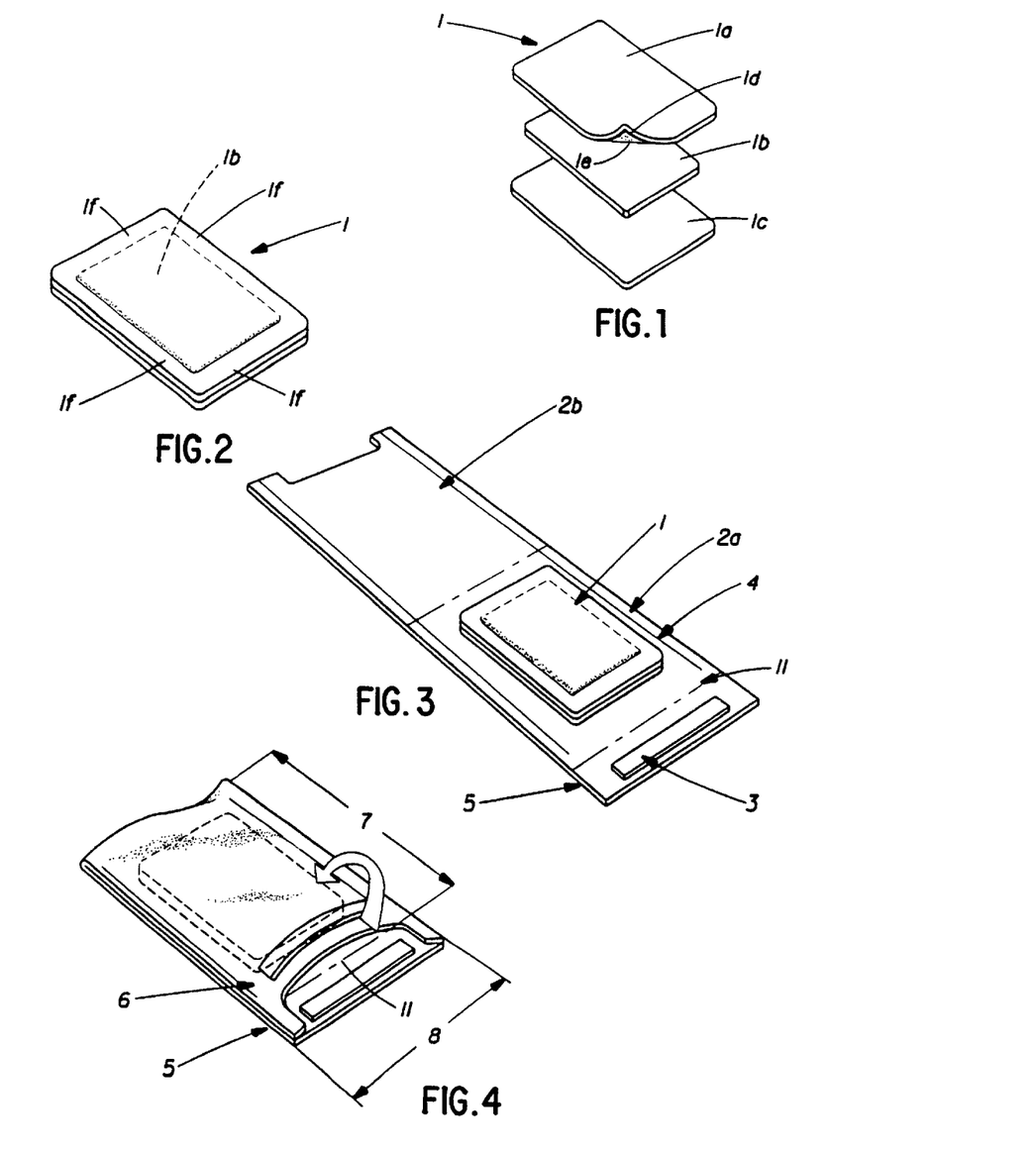
FIG. 1 is an exploded view of a sheet-form article (1) useful in the present invention in a pre-assembled state.
FIG. 2 is a perspective of the assembled cleaning/refreshing article (1).
FIG. 3 is a perspective of the article loosely resting on a notched, vapor-venting containment bag which is in a pre-folded condition.
FIG. 4 is a perspective of the article within the bag which is ready to receive fabrics or other articles to be treated in a hot air clothes dryer, or similar apparatus.

An absorbent carrier of the type used herein can comprise a simple absorbent sheet, preferably constructed from a hydroentangled mat of fibers as described more fully hereinafter. As shown in FIG. 1, a preferred article (1) of the present type can be assembled as a laminate comprising a topmost fibrous sheet (1a), an absorbent carrier sheet as the core (1b) and a bottommost fibrous sheet (1c). The combination of topsheet and bottomsheet comprises a "coversheet" which helps prevent water spotting of fabrics which come in contact with the article during the process of the invention.

The assembled laminate article (1) is shown in FIG. 2. FIG. 2 also shows the bond (1f) which extends around the periphery of the article. The purpose of this bond is to ensure that the absorbent carrier core maintains its original configuration relative to the coversheet when the article is being used in the manner of this invention. Stated simply, it has been discovered that if the absorbent sheet which comprises the core is not bonded to the "envelope" provided by the coversheet in-use, the carrier sheet tends to crumple and bunch-up inside the coversheet. This can interfere with the delivery of the cleaning/refreshment composition to the items being treated.

Moreover, it has also been discovered that it is not preferred to tightly bond the coversheet to the carrier sheet across the entire face of the carrier sheet. Tightly bonding the coversheet closely to the carrier sheet can allow some liquid transfer to occur through the coversheet. Accordingly, the carrier sheet is preferably bonded to the coversheet only in discrete areas. In one embodiment as shown in FIG. 2, this bonding is only around the periphery of the article. In another embodiment, spot-bonding at discrete areas across the face of the article can be employed. Various other bond patterns can be used. Preferably, the bonding is done at no more than about 50% of the area of the article, more preferably no more than about 10% of the area of the article, most preferably no more than about 1% of the area of the article.

Coversheet—The coversheets employed herein are distinguished from the carrier substrate sheets, inasmuch as the coversheets are relatively non-absorbent to the liquid cleaning/refreshment compositions as compared with the carrier sheets. The coversheets are constructed from hydrophobic fibers which tend not to absorb, "wick" or otherwise promote the transfer of fluids. While fluids can pass through the void spaces between the fibers of the coversheet, this occurs mainly when excessive pressure is applied to the article. Thus, under typical usage conditions the coversheet provides a physical barrier which keeps the absorbent carrier, which is damp from its load of aqueous cleaning/refreshment composition, from coming into direct contact with the fabrics being treated. Yet, the coversheet does allow vapor transfer of the cleaning/refreshment composition from the carrier through the coversheet and into the containment bag, and thence onto the fabrics being treated.

One type of coversheet herein comprises a fibrous, permeable nonwoven or woven fabric. Such nonwoven or woven fibrous coversheets offer advantages over formed-film type coversheets known in the catamenials art. For example, formed-film coversheets (as described hereinafter) are often manufactured by hydroforming processes which are particularly suitable with polymer films such as polyethylene. While polyethylene can be used herein, there is some prospect that, due to its lower melting point, high dryer temperatures can cause its softening and/or melting in-use. This is particularly true if the article herein were to be released from the containment bag and fall into the hot dryer drum. While it is possible to prepare formed-film topsheets using nylon, polyester or other heat resistant polymeric sheets, such manufacture becomes somewhat more difficult and, hence, more expensive.

It has now also been determined that the coversheet herein should be of a thickness which effectively provides the physical barrier function. Even though made from hydrophobic fibers, if the coversheet is too thin, fluid passage can occur under the intended usage conditions. Accordingly, it has now been determined that the thickness of the fibrous coversheet should preferably be at least about 7 mils (0.18 mm), preferably from about 8 mils (0.2 mm) to about 24 mils (0.6 mm). It has also been determined that the fibers used in the coversheet are preferably hydrophobic and preferably have a melting point above about 240° C.

Fibrous coversheets for use herein can readily be made from non-heat resistant fibers such as polyethylene. However, it has now been determined that preferred fibrous coversheets can be prepared using nylon (especially nylon-6), polyester, and the like, heat-resistant fibers which can withstand even inadvertent misuse in the present process. The flexible, cloth-like, permeable topsheets made therefrom are conventional materials in the art of nonwoven and woven fabric making, and their manufacture forms no part of the instant invention. Nonwoven fabrics for use as coversheets are available commercially from companies such as Reemay, Inc., Hickory, Tenn. Such coversheets also pick up solid dust particles, vagrant lint and other fibers from the fabrics being treated in the present process, thereby enhancing the overall clean/refreshed appearance of the fabrics following the treatment herein.

Such nonwoven or woven fibrous sheet materials can be used in a flat single layer or as multiple layers as the coversheet for the absorbent carrier core herein. In another embodiment, the absorbent core carrying the cleaning/refreshment composition is enrobed in a polyester or polyamide fibrous coversheet which has been ring rolled or otherwise crimped to provide three dimensional bulk. Optionally, this coversheet may be further covered by a second coversheet in an uncrimped configuration.

Such fibrous, preferably heat resistant and, most preferably, hydrophobic, coversheets thus provide various embodiments of the article herein. Suitable combinations can be employed, according to the desires of the manufacturer, without departing from the spirit and scope of the invention. If desired, the coversheet can be provided with macroscopic fenestrations through which the lint, fibers or particulate soils can pass, thereby further helping to entrap such foreign matter inside the article, itself.

A typical spun-bonded fibrous coversheet herein is commercially available from Reemay and has the following characteristics.

(a) Fabric Type—Non-woven, semi-dull, whitened homopolymer 100% virgin, spun-bonded polyester.
(b) Fiber Type—6.0 Denier straight, tri-lobal continuous fiber, copolymer polyester.

| Web Properties | Target | Range |
|---|---|---|
| a) Basis weight, roll average oz/yd$^2$ | 0.54 | 0.52 to 0.59 |
| b) Thickness | 8 mil | 7–8 mil |
| c) Fuzz level | | |

As measured by Reemay sled/drag method based on 0–5 scale. 5 being no fuzz level.

| Belt side | 2.5 | 5.0 | 1.8 |
| Jet side | 3.4 | 5.0 | 2.6 |

As noted above, another type of coversheet which can be used with the articles herein comprises the apertured "formed film" coversheets known in the art and from commercial use on catamenials. Apertured formed films are pervious to the liquid cleaning and/or refreshment compositions and vapors thereof, and yet non-absorbent. Thus, the surface of the formed film which is in contact with the fabrics remains relatively dry, thereby reducing water spotting and dye transfer. As with the fibrous coversheets, the apertured formed films capture and retain lint, fibrous matter such as pet hair, and the like, from the fabric being treated, thereby enhancing the cleaning/refreshment benefits afforded by the present articles. Suitable formed films are described in U.S. Pat. No. 3,929,135, entitled "Absorptive Structure Having Tapered Capillaries", issued to Thompson on Dec. 30, 1975; U.S. Pat. No. 4,324,246, entitled "Disposable Absorbent Article Having A Stain Resistant Coversheet", issued to Mullane and Smith on Apr. 13, 1982; U.S. Pat. No. 4,342,314, entitled "Resilient Plastic Web Exhibiting Fiber-Like Properties", issued to Radel and Thompson on Aug. 3, 1982; and U.S. Pat. No. 4,463,045, entitled "Macroscopically Expanded Three-Dimensional Plastic Web Exhibiting Non-Glossy Visible Surface and Cloth-Like Tactile Impression", issued to Ahr, Louis, Mullane and Ouellete on Jul. 31, 1984; U.S. Pat. No. 4,637,819 issued to Ouellette, Alcombright & Curro on Jan. 20, 1987; U.S. Pat. No. 4,609,518 issued to Curro, Baird, Gerth, Vernon & Linman on Sep. 2, 1986; U.S. Pat. No. 4,629,642 issued to Kernstock on Dec. 16, 1986; and EPO Pat. No. 0,165,807 of Osborn published Aug. 30, 1989; all of which are incorporated herein by reference. The apertures in such coversheets may be of uniform size or can vary in size, as disclosed in the foregoing published documents, which can be referred to for technical details, manufacturing methods, and the like. Such apertures may also vary in diameter in the manner of so-called "tapered capillaries". Such formed-film cover-sheets with tapered capillary apertures preferably are situated over the carrier sheet such that the smaller end of the capillary faces the carrier sheet and the larger end of the capillary faces outward. This helps prevent bulk liquid transfer, thereby minimizing water spotting on the fabrics being treated. In the main, apertures in the formed film coversheets used herein can have diameters in the range of from about 0.1 mm to about 1 mm, or as disclosed in the aforesaid patent references.

Carrier—When used in the in-dryer step of the present process, the cleaning/refreshment and sanitizing compositions are used in combination with an absorbent carrier. The carrier releasably contains the compositions. By "releasably contains" means that the compositions are effectively released from the carrier onto the soiled fabrics as part of the sanitizing non-immersion cleaning and/or fabric refreshment processes herein. This release occurs mainly by volatilization of the composition from the carrier substrate through the vapor-permeable coversheet, or by a combination of vapor and liquid transfer, although when treating fabrics bulk liquid transfer is desirably minimized by means of the coversheet, as disclosed hereinabove. It is to be understood, however, that when water spotting is of no particular concern to the user, the coversheet need not be employed with the absorbent carrier substrate.

The carrier can be in any desired form, such as powders, flakes, shreds, and the like. However, it is highly preferred that the carrier be in the form of an integral pad or sheet which substantially maintains its structural integrity throughout the process. Such pads or sheets can be prepared, for example, using well-known methods for manufacturing non-woven sheets, paper towels, fibrous batts, cores for bandages, diapers and catamenials, and the like, using materials such as wood pulp, cotton, rayon, polyester fibers, and mixtures thereof. Woven cloth pads may also be used, but are not preferred over non-woven pads due to cost considerations. Integral carrier pads or sheets may also be prepared from natural or synthetic sponges, foams, and the like.

The carriers are designed to be safe and effective under the intended operating conditions of the present process. The carriers must not be flammable during the process, nor should they deleteriously interact with the cleaning or refreshment composition or with the fabrics being cleaned. In general, non-woven polyester-based pads or sheets are quite suitable for use as the carrier herein.

The carrier used herein is most preferably non-linting. By "non-linting" herein is meant a carrier which resists the shedding of visible fibers or microfibers onto the fabrics being cleaned, i.e., the deposition of what is known in common parlance as "lint". A carrier can easily and adequately be judged for its acceptability with respect to its non-linting qualities by rubbing it on a piece of dark blue woolen cloth and visually inspecting the cloth for lint residues.

The non-linting qualities of sheet or pad carriers used herein can be achieved by several means, including but not limited to: preparing the carrier from a single strand of fiber; employing known bonding techniques commonly used with nonwoven materials, e.g., point bonding, print bonding, adhesive/resin saturation bonding, adhesive/resin spray bonding, stitch bonding and bonding with binder fibers.

The size of the carrier should not be so large as to be unhandy for the user. Typically, the dimensions of the carrier will be sufficient to provide a macroscopic surface area (both sides of the carrier) of at least about 360 $cm^2$, preferably in the range from about 360 $cm^2$ to about 3000 $cm^2$. For example, a generally rectangular carrier may have the dimensions (X-direction) of from about 10 cm to about 35 cm, and (Y-direction) of from about 18 cm to about 45 cm.

The carrier is intended to contain a sufficient amount of the cleaning/refreshment compositions to be effective for their intended purpose. The capacity of the carrier for such compositions will vary according to the intended usage. For example, pads or sheets which are intended for a single use in cleaning/refreshing/sanitizing fabrics will require less capacity than such pads or sheets which are intended for multiple uses. For a given type of carrier the capacity for the cleaning or refreshment composition will vary mainly with the thickness or "caliper" (Z-direction; dry basis) of the sheet or pad. For purposes of illustration, typical single-use polyester sheets used herein will have a thickness in the range from about 0.1 mm to about 0.7 mm and a basis weight in the range from about 30 $g/m^2$ to about 100 $g/m^2$. Typical multi-use polyester pads herein will have a thickness in the range from about 0.2 mm to about 1.0 mm and a basis weight in the range from about 40 $g/m^2$ to about 150 $g/m^2$. Open-cell sponge sheets will range in thickness from about 0.1 mm to about 1.0 mm. Of course, the foregoing dimensions may vary, as long as the desired quantity of the cleaning or refreshment composition is effectively provided by means of the carrier.

A preferred carrier herein comprises a binderless (or optional low binder), hydroentangled absorbent material, especially a material which is formulated from a blend of cellulosic, rayon, polyester and optional bicomponent fibers. Such materials are available from Dexter, Non-Wovens Division, The Dexter Corporation as HYDRASPUN®, especially Grades 10244 and 10444. The manufacture of such materials forms no part of this invention and is already disclosed in the literature. See, for example, U.S. Pat. No. 5,009,747, Viazmensky, et al., Apr. 23, 1991 and U.S. Pat. No. 5,292,581, Viazmensky, et al., Mar. 8, 1994, incorporated herein by reference. Preferred materials for use herein have the following physical properties.

Dexter Sheet Grade 10244

|  | Units | Targets | Ranges |
|---|---|---|---|
| Basis Weight | gm/m$^2$ | 55 | 35–75 |
| Thickness | microns | 355 | 100–1500 |
| Density | gm/cc | 0.155 | 0.1–0.25 |
| Dry Tensile | gm/25 mm | | |
| MD | | 1700 | 400–2500 |
| CD | | 650 | 100–500 |
| Wet Tensile | gm/25 mm | | |
| MD* | | 700 | 200–1250 |
| CD* | | 300 | 100–500 |
| Brightness | % | 80 | 60–90 |
| Absorption Capacity | % | 735 | 400–900 ($H_2O$) |
| Dry Mullen | gm/cm$^2$ | 1050 | 700–1200 |

*MD - machine direction; CD - cross direction

As disclosed in U.S. Pat. No. 5,009,747 and 5,292,281, the hydroentangling process provides a nonwoven material which comprises cellulosic fibers, and preferably at least about 5% by weight of synthetic fibers, and requires less than 2% wet strength agent to achieve improved wet strength and wet toughness.

It has been discovered that this hydroentangled carrier material provides an additional, unexpected benefit due to its resiliency. In-use, the articles herein are designed to function in a substantially open configuration. However, the articles may be packaged and sold to the consumer as sheets which are in a folded configuration. It has been discovered that the carrier sheets made from conventional materials tend to undesirably revert to their folded configuration in-use. Indeed, this tendency to re-fold along the original fold lines seems to be exacerbated by the coversheet materials used herein. While the hydroentangled materials used to form the carrier sheet herein have less tendency to re-fold during use than do other carrier materials, it has been determined experimentally that up to 60% refold does seem to occur under intended usage conditions when the fibrous coversheet is present. In some instances, and especially with certain types of fabrics, this can be problematic, inasmuch as wet strikes can occur along the sharp fold lines, presumably due to pressure forcing the liquid composition through the fibrous coversheet.

However, it has now been determined that by providing holes or otherwise fenestrating the carrier sheet, this tendency to re-fold is substantially lessened even when the coversheet is used in the non-immersion cleaning/refreshment/sanitization process of the present invention. Thus, in a preferred mode of practicing the present invention a plurality of holes, slits, or other fenestrations are placed in the carrier sheet to help minimize re-fold when the article is used. The number and placement of the holes or other fenestrations can be determined by routine experimentation. Example I hereinafter gives the size and number of circular holes which are useful for an article of the size and with the load of cleaning/refreshment composition described therein.

Cleaning/Refreshing Compositions—The user of the present process can be provided with various cleaning/refreshing compositions to use in the practice the invention. One problem associated with known fabric treatment compositions is their tendency to leave visible residues on fabric surfaces. Such residues are problematic and are preferably to be avoided herein since the present process does not involve conventional immersion or rinse steps. Accordingly, the compositions used herein should, most preferably, be substantially free of various gelling agents, polyacrylate-based emulsifiers, polymeric anti-static agents, inorganic builder salts and other residue-forming materials, except at low levels of about 0.1 %-0.3%, and preferably 0%, of the final compositions. Water used in the compositions should preferably be distilled, deionized or otherwise rendered free of residue-forming materials. Stated otherwise the compositions herein should preferably be formulated so as to leave substantially no visible residue on fabrics or other solid surfaces being treated according to the practice of this invention.

Accordingly, in a preferred aspect of this invention there are provided cleaning/refreshment and sanitizing compositions which are substantially free of quantities of materials which are sufficient to leave visible residues on the treated fabrics.

Aqueous Compositions For Cleaning/Refreshing or Pre-Treating Compositions (a) Water—The preferred, low residue compositions herein may comprise from about 90%, preferably from about 95.5% to about 99.9%, by weight, of water.

(b) Antimicrobial agents—antimicrobial agents can be selected from the group consisting of 5-chloro-2-(2,4-dichlorophenoxy)phenol, trichlorocarbanalide, hydrogen peroxide, other oxygen bleaches, 4-chloro-3,5-dimethylphenol, iodine/iodophors, chlorhexidine, phenols, phospholipids, thymol, eugeniol, geraniol, oil of lemon grass, limonene and mixtures thereof. A second antimicrobial agent can be selected from the group consisting of alkyl alkoxy sulfates, linear alkyl benzene sulfonates, amine oxides, polyhydroxy fatty acid amides, ethoxylated alcohols, diamines, amides, alkyl polyglucosides, betaines, and mixtures thereof.

(c) Surfactant—The compositions herein may optionally comprise, in addition to the antimicrobial agents listed above, from about 0.05% to about 2%, by weight, of surfactants, such as MgAES and $NH_4AES$, amine oxides, ethoxylated alcohols or alkyl phenols, alkyl sulfates, and mixtures thereof.

(d) Optionals—The compositions herein may comprise minor amounts of various optional ingredients, including bleach stabilizers, perfumes, and the like. If used, such optional ingredients will typically comprise from about 0.05% to about 2%, by weight, of the compositions, having due regard for residues on the cleaned fabrics.

(e) Chelator—Compositions which contain hydrogen peroxide or other oxygen bleaches will also typically contain a chelating agent. The chelating agent is selected from those which, themselves, are stable in aqueous hydrogen peroxide and which stabilize the hydrogen peroxide by chelating vagrant metal ions. Such chelating agents are typically already present at low, peroxide-stabilizing amounts (0.01–1%) in commercial sources of hydrogen peroxide. A variety of phosphonate chelators are known in stabilizing hydrogen peroxide. The amino phosphonates are especially useful for this purpose. Various amino phosphonates are available as under the DEQUEST® trade name from the Monsanto Company, St. Louis, Mo. Representative, but non-limiting, examples include ethylenediamine tetrakis (methylene phosphonic) acid, diethylenetriamine penta(methylene phosphonic) acid, and the water-soluble salts thereof. Amino tris (methylene phosphonic) acid or its water-soluble salts (as DEQUEST 2000®) is a preferred chelator. The pH range of the compositions helps provide stability to the hydrogen peroxide and is typically in the acid-slightly basic range from about 3 to about 8, preferably about 6 to about 7.

Surfactants—Nonionics such as the ethoxylated $C_{10}$–$C_{16}$ alcohols, e.g., NEODOL 23–6.5, can be used in the compositions. The alkyl sulfate surfactants which may be used herein as cleaners and to stabilize aqueous compositions are the $C_8$–$C_{18}$ primary ("AS"; preferred $C_{10}$–$C_{14}$, sodium salts), as well as branched-chain and random $C_{10}$–$C_{20}$ alkyl sulfates, and $C_{10}$–$C_{18}$ secondary (2,3) alkyl sulfates of the formula $CH_3(CH_2)_x(CHOSO_3^-M^+)$ $CH_3$ and $CH_3$ $(CH_2)_y$ $(CHOSO_3^-M^+)$ $CH_2CH_3$ where x and (y+1) are integers of at least about 7, preferably at least about 9, and M is a water-solubilizing cation, especially sodium, as well as unsaturated sulfates such as oleyl sulfate. Alkyl ethoxy sulfate (AES) surfactants used herein are conventionally depicted as having the formula $R(EO)_xSO_3Z$, wherein R is $C_{10}$–$C_{16}$ alkyl, EO is —$CH_2CH_2$—O—, x is 1–10 and can include mixtures which are conventionally reported as averages, e.g., $(EO)_{2.5}$, $(EO)_{6.5}$ and the like, and Z is a cation such as sodium ammonium or magnesium (MgAES). The $C_{12}$–$C_{16}$ alkyl dimethyl amine oxide surfactants can also be used. A preferred mixture comprises $MgAE_1S/C_{12}$ dimethyl amine oxide at a weight ratio of about 10:1. Other surfactants which improve phase stability and which optionally can be used herein include the polyhydroxy fatty acid amides, e.g., $C_{12}$–$C_{14}$ N-methyl glucamide. AS stabilized compositions preferably comprise 0.1%–0.5%, by weight, of the compositions herein. MgAES and amine oxides, if used, can comprise 0.01%-2%, by weight, of the compositions. The other surfactants can be used at similar levels.

Having due regard to the foregoing considerations, the following illustrates the various other ingredients which can be used in the liquid compositions herein, but is not intended to be limiting thereof.

Other Optionals—In addition to the water and the surfactants disclosed above, liquid compositions used herein may comprise various optional ingredients, such as perfumes, preservatives, brighteners, salts for viscosity control, pH adjusters or buffers, and the like. The following illustrates preferred ranges for cleaning compositions for use herein, but is not intended to be limiting thereof.

| Ingredient | % (wt.) Formula Range |
|---|---|
| Antimicrobial Agent | 0–3 |
| Surfactant | 0–2 |
| Perfume | 0–1.5 |
| Water | Balance | pH range from about 6 to about 8.

Preferred compositions for use in the in-dryer cleaning/refreshment/sanitization process herein are as follows.

| Ingredient | % (wt.) | Range (% wt.) |
|---|---|---|
| Water | 98.5 | 95.1–99.9 |
| Antimicrobial Agent | 0.1 | 0.05–3 |
| Perfume | 0.5 | 0–1.5 |
| Surfactant* | 0.5 | 0.05–2.0 |
| Ethanol or Isopropanol | 0 | Optional to 4% |

*Especially ethoxylated alcohols, as disclosed herein. The fabric refreshment compositions may also contain anionic surfactants. Such anionic surfactants are well-known in the detergency arts. Commercial surfactants available as TWEEN ®, SPAN ®, AEROSOL OT ® and various sulfosuccinic esters are especially useful herein.

Perfume—It has been determined that higher molecular weight, high boiling point, malodorous chemicals tend to be retained on the fabrics, at least to some degree. These malodors can be overcome, or "masked", by perfumes. Accordingly, it will be appreciated that the perfumer should select at least some perfume chemicals which are sufficiently high boiling that they are not entirely lost during the process. A wide variety of aldehydes, ketones, esters, acetals, and the like, perfumery chemicals which have boiling points above about 50° C., preferably above about 85° C., are known. Such ingredients can be delivered to the fabrics being treated by means of the carrier substrate herein during the processes herein, thereby helping to reduce the user's perception of malodors. Non-limiting examples of perfume materials with relatively high boiling components include various essential oils, resinoids, and resins from a variety of sources including but not limited to orange oil, lemon oil, patchouli, Peru balsam, Olibanum resinoid, styrax, labdanum resin, nutmeg, cassia oil, benzoin resin, coriander, lavandin and lavender. Still other perfume chemicals include phenyl ethyl alcohol, terpineol and mixed pine oil terpenes, linalool, linalyl acetate, geraniol, nerol, 2-(1,1-dimethylethyl)-cycldhexanol acetate, orange terpenes and eugenol. Of course, lower boiling materials can be included, with the understanding that some loss will occur due to venting.

Vapor Venting Bag—The compositions are loaded on the carrier substrate which is preferably encased in the coversheet and the finished article is placed in a bag environment for use in a heated operating clothes dryer, or the like, to sanitize the fabrics and to remove malodors from the fabrics as a dry cleaning alternative or "fabric refreshment" process. The warm, humid environment created inside this bag volatilizes the aqueous cleaning/refreshing composition resulting in a sterilization of the fabric articles within and removal of malodor components in the manner of a "steam distillation" process, and moistens fabrics and the soils thereon.

In addition to the desired sanitization effect, the moistening of fabrics with the volatilized cleaning/refreshing composition can loosen pre-set wrinkles. But it has been discovered that overly wet fabrics can experience setting of new wrinkles during the drying stage toward the end of the dryer cycle. Proper selection of the amount of water used in the process and, importantly, proper venting of the bag in the present manner can minimize wrinkling. Moreover, if the bag is not vented, the volatilized malodorous materials removed from the fabrics can undesirably be re-deposited thereon.

In a highly preferred mode, the process of the present invention employs a vapor-venting containment bag. The bag is preferably designed for multiple uses and reuses, and is especially adapted for use by the consumer in any conventional hot air clothes dryer apparatus, such as those found in the home or in commercial laundry/cleaning establishments. The bag is designed to vent water and other vapors (including malodorous materials) which emanate from within the bag when used in the manner described herein. The vapors released from the bag are then exhausted through the air vent of the dryer apparatus.

The design of the venting ability of the bag achieves a proper balance of the above effects. A tightly-sealed, vapor impermeable "closed" bag will not release a sufficient amount of vapor which will overly moisten the fabrics, resulting in a reduction in the killing of microbials. An overly "open" bag design will not sufficiently moisten the fabrics or soils to kill the microbials. Further, the bag must be "closed" enough to billow and create a void volume under water vapor pressure, wherein the fabrics can tumble freely within the bag and be exposed to the vapors.

The bag is designed with sufficient venting to trap a portion of water vapors (especially early in the dryer cycle) but to allow most of the water to escape by the end of the cycle. Said another way, the rate of vapor release is, preferably, optimized to secure a balance of vapor venting and vapor trapping. A preferred bag design employs a water vapor impermeable film such as nylon, with a the closure flap (preferably with a hook-and-loop VELCRO®-type fastener) like that of a large envelope. The degree of slack in the fold-over portion of the closure flap can be varied to provide a vapor-venting air gap or partial opening which controls the rate of vapor venting from of the bag. In another mode, a notch is cut along the edge of the side wall opposite the flap to further adjust the venting. The fastener devices shown in the Figures run only partly along the closure, thereby allowing venting to also occur at the lateral edges of the closure.

As described more fully hereinafter, the preferred venting bag is provided with a vapor-venting closure which provides one or more gaps through which vapors are released from the bag, in-use. In a preferred embodiment, the size of this gap is selected to provide controlled vapor release from the bag under the indicated operating conditions. While other gap sizes and operating conditions can be used, a preferred balance between vapor containment within the bag—to perform the sanitization of the fabrics along with the cleaning/refreshment function and vapor release from the bag—has now been determined using the principles disclosed hereinafter.

Alternatively, the bag can be provided with a series of holes or other fenestrations which provide vapor venting. However, such venting is not as effective as the vapor-venting closure.

In one mode, the present invention employs a vapor-venting containment bag comprising an open end, a closed end and flexible side walls having inner and outer surfaces, the open end of said bag having a section of one side wall extending beyond said open end to provide a flexible flap, said flap having first fastening device affixed thereto, said flap being foldable to extend over a portion of the outside surface of the opposing side wall, said flap being affixable to the outer surface of the opposing wall of the bag by engaging said first fastening device on the inside face of the flap with a second fastening device present on the outside face of said opposing side wall, said first and second fastening devices, when thus engaged, forming a fastener, thereby providing a closure for the open end of the bag. Said first and second fastening devices are disposed so as, when engaged, to provide vapor-venting along said closure, especially at the lateral edges of the closure. The bag herein is most preferably formed from film which is heat resistant up to at least about 204° C.–260° C. Nylon is a preferred film material for forming the bag. In another embodiment, the edge of one wall of the bag is notched along a substantial portion of its width to facilitate and optimize vapor venting.

In an alternate mode, the flap can be folded to provide the closure, tucked inside the opposing side wall, and secured there by a fastener. In this mode, vapors are vented along the closure and especially at the lateral edges of the closure. In yet another mode, the side walls are of the same size and no flap is provided. Fastening devices placed intermittently along portions of the inner surfaces of the side walls are engaged when the lips of the side walls are pressed together to provide closure. One or more vapor-venting gaps are formed in those regions of the closure where no fastening device is present.

While the fastening devices herein can comprise chemical adhesives, the bag is preferably designed for multiple uses. Accordingly, reusable mechanical fasteners are preferred for use herein. Any reusable mechanical fastener or fastening means can be used, as long as the elements of the fastener can be arranged so that, when the bag is closed and the fastener is engaged, a vapor-venting closure is provided. Non-limiting examples include: bags wherein said first and second fastening devices, together, comprise a hook and loop (VELCRO®-type) fastener; hook fasteners such as described in U.S. Pat. No. 5,058,247 to Thomas & Blaney issued Oct. 22, 1991; bags wherein said first and second fastening devices, together, comprise a hook and string type fastener; bags wherein said first and second fastener devices, together, comprise an adhesive fastener; bags wherein said first and second fastening devices, together, comprise a toggle-type fastener; bags wherein said first and second fastening devices, together, form a snap-type fastener; as well as hook and eye fasteners, ZIP LOK®-style fasteners, zipper-type fasteners, and the like, so long as the fasteners are situated so that vapor venting is achieved. Other fasteners can be employed, so long as the vapor-venting is maintained when the bag is closed, and the fastener is sufficiently robust that the flap does not open as the bag and its contents are being tumbled in the clothes dryer. The fastening devices can be situated that the multiple vapor-venting gaps are formed along the closure, or at the lateral edges, or so that the gap is offset to one end of the closure. In yet another embodiment, both ends of the bag are provided with a vapor venting closure.

Preferred bags of the foregoing type which are designed for use in a conventional U.S.-style automatic, in-home hot air clothes dryer will have a volume in the range from about 10,000 $cm^3$ to about 25,000 $cm^3$.

The invention also employs a process for cleaning or refreshing fabrics by contacting said fabrics with a fabric cleaning/refreshing composition comprising water in the aforesaid vapor-venting containment bag. This process is conveniently carried out in a hot air clothes dryer, or the like. Those skilled in the art will recognize that hot air clothes dryers operate at temperatures sufficient to vaporize water, that is, from about 40° C. to about 250° C., preferably, from about 40° C. to about 150° C.; whereby the fabrics and vapor venting bag are sterilized, and malodors present on the fabrics are vented from the bag by means of the vapor-venting closure.

The following is intended to assist the formulator in the manufacture and use of vapor-venting bags in the manner of this invention, but is not intended to be limiting thereof.

Bag Dimensions—FIG. 4 shows the overall dimensions of a notched bag: i.e., length (7) to fold line 27⅝ inches (70.2 cm); width (8) of bag 26 inches (66 cm), with a flap to the base of the fold line (11) of 2⅜ inches (6 cm). In the Tests reported hereinafter, this bag is referred to by its open dimensions as "26 in.×30 in." (66.04 cm×76.20 cm).

Figure 5:
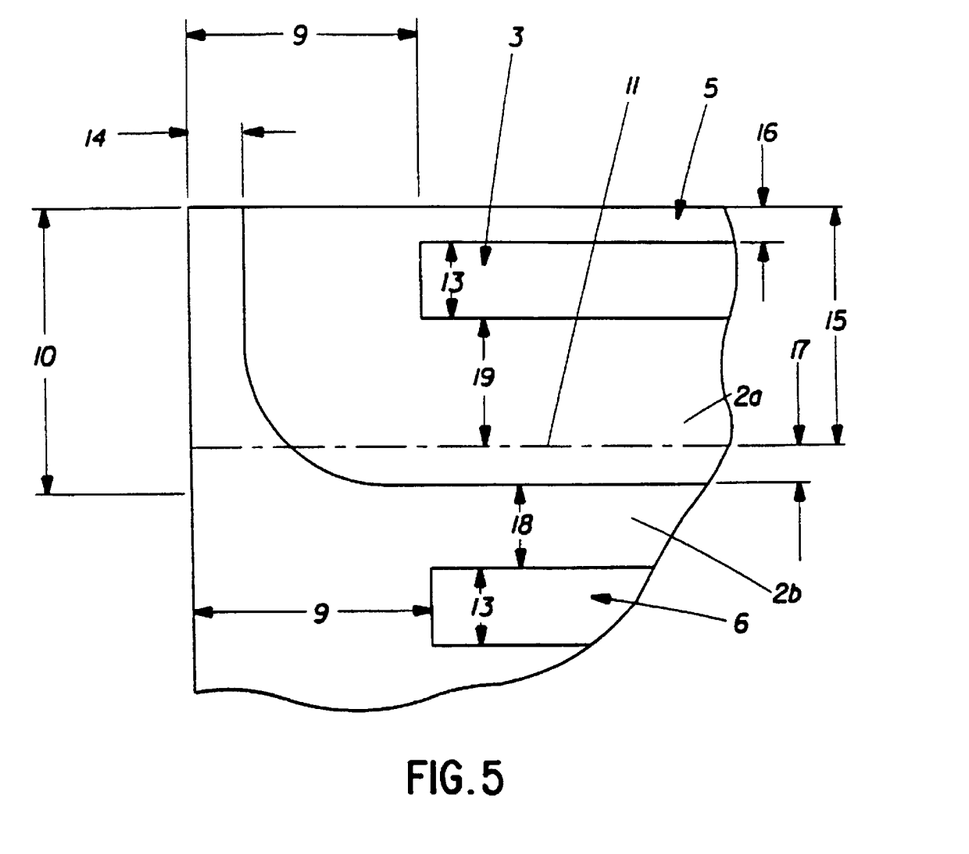
FIG. 5 is a partial view of the notched wall of the bag and its disposition relative to the closure flap.

FIG. 5 gives additional details of the positioning of the various elements of the notched bag. In this embodiment, all dimensions are the same for both the left hand and right hand sides of the bag. The dimensions herein are for an opened bag which is about 30 inches (76.2 cm) in overall length (including the flap) and about 26 inches (66 cm) wide. The distance (9) from the lateral edge of the bag to the outermost edge of the fastening device (3) located on the inside of the flap (5) is about 2 inches (5 cm). In this embodiment, the fastening device (3) on the inside of wall (2a) comprises the loop portion of a VELCRO®-type strip whose width (13) is about 0.75 inches (1.9 cm) and whose total length is about 22 inches (55.9 cm). Fastening device (6) is similarly situated on the outside of wall 2(b) and comprises the hook portion of a ¾ inch (1.9 cm) VELCRO®-type strip. Distance (9) can be decreased or increased to decrease or increase venting at the edges of the flap when the bag is closed and the fastener is engaged. The distance (10) between the uppermost edge of the flap and the base of the notch is about 2⅞ inches (7.3 cm). The distance (14) between the lateral edge of the bag and the lateral edge of the notch is about 0.25 inches (0.64 cm). The distance (15) between the uppermost edge of the flap and the fold (11) is about 2⅜ inches (6 cm). The distance (16) between the uppermost edge of the flap and the leading edge of the VELCRO®-type strip (3) affixed to the flap is about ⅜ inches (0.95 cm). The distance (17) between fold (11) and the lowermost edge of the notch is about ½ inch (1.27 cm). This distance also can be varied to decrease or increase vapor venting. A range of 0.25–1.5 inches (0.64–3.81 cm) is typical. The distance (18) between the uppermost edge of the VELCRO®-type strip (6) and the bottom edge of the notch is about ¾ inches (1.9 cm). The distance (19) between the bottommost edge of the VELCRO (®-type strip (3) and the fold (11) is about 1¼ inches (3.17 cm).

Figure 6:
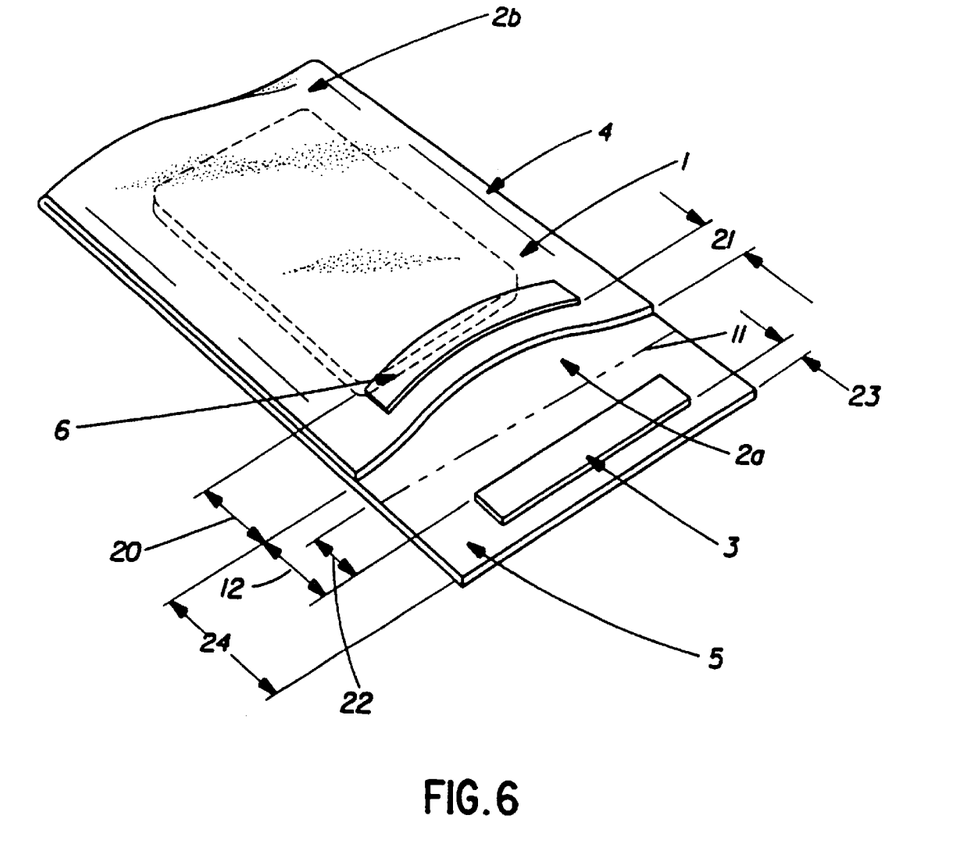
FIG. 6 is a perspective of an un-notched vapor-venting bag containing a loose sheet-form article used in the manner of the present invention.

FIG. 6 gives additional details of the dimensions of an un-notched envelope bag of the foregoing overall size comprising sidewalls (2a)) and (2b). Again, each VELCRO®-type strip (3) and (6) is about ¾ inches (1.9 cm) in width and about 22 inches (55.9 cm) in length. Each strip is positioned so as to be inboard from each of the lateral edges of the finished bag wall and flap by about 2 inches (5 cm). The distance (12) between the leading edge of the sidewall (2b) to the base edge of the fastener strip (3) on the flap portion of the bag is about 2½ inches (6.35 cm). The distance (20) between the base edge of the fastener strip (6) to the leading edge of the sidewall (2b) is about 2.25 inches (5.7 cm). The distance (21) between the leading edge of the fastener strip (6) to the leading edge of the sidewall is about 1⅜ inches (3.5 cm). The distance (22) between fold (11) and the base edge of the fastener strip (3) is about 2 inches (5 cm). The distance (23) between the leading edge of fastener strip (3) and the uppermost edge of the flap which is an extension of sidewall (2a)) is about 0.25 inches (0.64 cm). Distance (24) is about 3⅝ inches (9.2 cm). As in the foregoing notched bag, the positioning and length of the fasteners can be adjusted to decrease or increase venting.

The construction of the preferred, heat-resistant vapor-venting bag used herein to contain the fabrics in a hot air laundry dryer or similar device preferably employs thermal resistant films to provide the needed temperature resistance to internal self-sealing and external surface deformation sometimes caused by overheated clothes dryers. In addition, the bags are resistant to the chemical agents used in the cleaning or refreshment compositions herein. By proper selection of bag material, unacceptable results such as bag melting, melted holes in bags, and sealing of bag wall-to-wall are avoided. In a preferred mode, the fastener is also constructed of a thermal resistant material. As shown in FIGS. 4 and 6, in one embodiment, 1 to 3 mil (0.025–0.076 mm) heat-resistant Nylon-6 film is folded and sealed into a containment bag. Sealing can be done using standard impulse heating equipment. In an alternate mode, a sheet of nylon is simply folded in half and sealed along two of its edges. In yet another mode, bags can be made by air blowing operations. The method of assembling the bags can be varied, depending on the equipment available to the manufacturer and is not critical to the practice of the invention.

The dimensions of the containment bag can vary, depending on the intended end-use. For example, a relatively smaller bag can be provided which is sufficient to contain one or two silk blouses. Alternatively, a larger bag suitable for handling a man's suit can be provided. Typically, the bags herein will have an internal volume of from about 10,000 $cm^3$ to about 25,000 $cm^3$. Bags in this size range are sufficient to accommodate a reasonable load of fabrics (e.g., 0.2–5 kg) without being so large as to block dryer vents in most U.S.-style home dryers. Somewhat smaller bags may be used in relatively smaller European and Japanese dryers.

The bag herein is preferably flexible, yet is preferably durable enough to withstand multiple uses. The bag also preferably has sufficient stiffness that it can billow, in-use, thereby allowing its contents to tumble freely within the bag during use. Typically, such bags are prepared from 0.025 mm to 0.076 mm (1–3 mil) thickness polymer sheets. If more rigidity in the bag is desired, somewhat thicker sheets can be used.

In addition to thermally stable "nylon-only" bags, the containment bags herein can also be prepared using sheets of co-extruded nylon and/or polyester or nylon and/or polyester outer and/or inner layers surrounding a less thermally suitable inner core such as polypropylene. In an alternate mode, a bag is constructed using a nonwoven outer "shell" comprising a heat-resistant material such as nylon or polyethylene terephthalate and an inner sheet of a polymer which provides a vapor barrier. The non-woven outer shell protects the bag from melting and provides an improved tactile impression to the user. Whatever the construction, the objective is to protect the bag's integrity under conditions of thermal stress at temperatures up to at least about 400–500° F. (204° C. to 260° C.). Under circumstances where excessive heating is not of concern, the bag can be made of polyester, polypropylene or any convenient polymer material.

Vapor Venting Evaluation—In its broadest sense, the preferred vapor-venting containment bag used herein is designed to be able to vent at least about 40%, preferably at least about 60%, up to about 90%, preferably no more than about 80%, by weight, of the total moisture introduced into the bag within the operating cycle of the clothes dryer or other hot air apparatus used in the process herein. (Of course most, if not all, of organic cleaning solvents, if any, will also be vented during together with the water. However, since water comprises by far the major portion of the cleaning/refreshment compositions herein, it is more convenient to measure and report the venting as water vapor venting.)

It will be appreciated by those knowledgeable about the operation of hot air clothes dryers and similar apparatus that the rate of venting will usually not be constant over the entire operating cycle. All dryers have a warm-up period at the beginning of the operating cycle, and this can vary according to the specifications of the manufacturer. Most dryers have a cool-down period at the end of the operating cycle. Some venting from the containment bag can occur during these warm-up and cool-down periods, but its rate is generally less than the venting rate over the main period of the drying cycle. Moreover, even during the main period of the cycle, many modern dryers are constructed with thermostat settings which cause the air temperature in the dryer to be increased and decreased periodically, thereby preventing overheating. Thus, an average, rather than constant, dryer operating temperature in the target range of from about 50° C. to about 85° C. is typically achieved.

Moreover, the user of the present containment bag may choose to stop the operation of the drying apparatus before the cycle has been completed. Some users may wish to secure fabrics which are still slightly damp so that they can be readily ironed, hung up to dry, or subjected to other finishing operations.

Apart from the time period employed, the Vapor-Venting Equilibrium ("VVE") for any given type of vapor-venting closure will depend mainly on the temperature achieved within the dryer—which, as noted above, is typically reported as an average "dryer air temperature". In point of fact, the temperature reached within the containment bag is more significant in this respect, but can be difficult to measure with accuracy. Since the heat transmittal through the walls of the bag is rather efficient due to the thinness of the walls and the tumbling action afforded by conventional clothes dryers, it is a reasonable approximation to measure the VVE with reference to the average dryer air temperature.

Moreover, it will be appreciated that the vapor-venting from the containment bag should not be so rapid that the aqueous cleaning/refreshment composition does not have the opportunity to moisten the fabrics being treated and to mobilize and remove the soils/malodors therefrom. However, this is not of practical concern herein, inasmuch as the delivery of the composition from its carrier substrate onto the fabrics afforded by the tumbling action of the apparatus occurs at such a rate that premature loss of the composition by premature vaporization and venting is not a significant factor. Indeed, the preferred bag herein is designed to prevent such premature venting, thereby allowing the liquid and vapors of the cleaning/refreshment composition to remain within the bag for a period which is sufficiently long to perform its intended functions on the fabrics being treated.

The following Vapor-Venting Evaluation Test (VVET) illustrates the foregoing points in more detail. Larger or smaller containment bags can be used, depending on the volume of the dryer drum, the size of the fabric load, and the like. As noted above, however, in each instance the containment bag is designed to achieve a degree of venting, or VVE "score", of at least about 40% (40 VVE), preferably at least about 60% (60 VVE), up to about 90% (90 VVE).

VAPOR-VENTING EVALUATION TEST

Materials

Envelope or "Standard", i.e., Control Containment Bag to be evaluated for VVE. Carrier Substrate (15"×11"; 38.1 cm×27.9 cm) HYDRASPUN® carrier substrate sheet from Dexter with (10444) or without (10244) Binder Wool Blouse: RN77390, Style 12288, Weight approx. 224 grams Silk Blouse: RN40787, Style 0161, Weight approx. 81 grams Rayon Swatch: 45"×17" (114.3 cm×43.2 cm), Weight approx. 60 grams Pouch: 5"×6.375" (12.7 cm×16.2 cm) to contain the Carrier Substrate and water De-ionized Water; Weight is variable to establish VVE.

Pretreatment of Fabrics

1. The wool, silk, and rayon materials are placed in a Whirlpool dryer (Model LEC7646DQO) for 10 minutes at high heat setting, with the heating cycle ranging from about 140° F.–165° F. to remove moisture picked up at ambient condition.
2. The fabrics are then removed from the dryer and placed in sealed nylon or plastic bags (minimum 3 mil. thickness) to minimize moisture pick up from the atmosphere.

Test Procedure

1. Water of various measured weights from 0 to about 40 grams is applied to the carrier substrate a minimum of 30 minutes before running a vented bag test. The substrate is folded, placed in a pouch and sealed.
2. Each fabric is weighed separately and the dry weights are recorded. Weights are also recorded for the dry carrier substrate, the dry pouch containing the substrate, and the dry containment bag being evaluated.
3. Each garment is placed in the bag being evaluated for vapor venting along with the water-containing substrate (removed from its pouch and unfolded).
4. The bag is closed without expressing the air and placed in the Whirlpool Dryer for 30 minutes at the high heat setting, with tumbling per the standard mode of operation of the dryer.
5. At the end of 30 minutes the bag is removed from the dryer and each fabric, the carrier substrate, the bag and the pouch are weighed for water weight gain relative to the dry state. (A possible minor loss in weight for the containment bag due to dryer heat is ignored in the calculations.)
6. The weight gain of each garment is recorded as a percent of the total moisture applied to the carrier substrate.
7. The remaining unmeasured moisture divided by the total moisture is recorded as percent vented from the dryer bag.
8. When a series of total applied moisture levels are evaluated, it is seen that above about 15–20 grams of water the % vented becomes essentially constant, and this is the Vapor-Venting Equilibrium value, or VVE, for the particular bag venting design.

It can be seen from examining a series of VVET results at various initial moisture levels that the water at lower initial levels is being disproportionately captured by the garment load, the headspace, and the nylon bag, such that venting of water and volatile malodors begins in earnest only after the VVE value is achieved. Since this occurs only when about 15–20 grams or more of water is initially charged, it is seen that a VVE of greater than about 40 is needed to avoid excessive wetting of garments, leading to unacceptable wet-setting of wrinkles, as discussed herein.

Pre-Treating Step—The overall process herein optionally comprises a pre-treating step which can also serve as a spot removal step on isolated, heavily stained areas of the fabric. This pre-treating step can be effective in neutralizing certain malodor causing chemicals such as isovalaric acid, short chain amines and short chain sulfur compounds. These compounds are known to be the by-products of bacterial "digestion" of human perspiration components.

The pre-treating step preferably comprises the step of applying a pre-treating composition to at least a portion of the fabric, wherein the pre-treating composition comprises an antimicrobial agent selected from the group consisting of 5-chloro-2-(2,4-dichlorophenoxy)phenol, trichlorcarbanilide, hexachlorophene, chlorhexadine, o-phenylphenol, benzylquaternium salts and mixtures thereof. The pre-treating composition preferably further comprises water, a minor amount of a solvent such as Butoxy Propoxy Propanol (BPP), and surfactants such as those discussed above. The pre-treating composition can be rubbed into the fabric using the tip of the bottle that contains the pre-treating composition or with an implement. The excess pre-treating composition can be absorbed by an absorbent stain receiver that is preferably placed on the side of the fabric opposite to the side that receives the pre-treating composition. The absorbent stain receiver can be a conventional paper towel, a thermally bonded air laid sheet, an absorbent polymeric foam or the like.

Following this localized pretreating step, the entire fabric can be cleaned/refreshed in the vapor-venting containment bag. This latter step provides a marked improvement in the overall appearance and refreshment of fabrics, especially with respect to the near absence of malodors and wrinkles, as compared with untreated fabrics.

PROCESS COMPONENTS

The use of the article with the vapor-venting bag, the compositions and the processes of this invention are described in more detail hereinafter. Such disclosure is by way of illustration and not limitation of the invention herein. The definitional terms used herein have the following meanings.

FIG. 3 illustrates one form of a pre-formed, notched containment bag in an open configuration with the loose article (1), first side wall (2a)), second side wall (2b), first fastening device (3), side seal (4) for the bag and flexible flap (5). In use, flexible flap (5) is folded along fold line (11) to provide the vapor-venting closure for the bag.

FIG. 4 shows the "envelope-style" notched bag in a finished configuration and containing the loose article (1). In-use, the fabrics to be cleaned/refreshed are placed in the bag with the article (1) and flap (5) is folded along fold line (11) to engage first fastening device (3) with the opposing second fastening device (6) to fasten the flap, thereby providing a vapor-venting closure which is sufficiently stable to withstand tumbling in a hot air clothes dryer or similar device.

FIG. 5 shows a cut-away view of the corner of the notched containment bag illustrating the interior of the first side wall (2a)) and second side wall (2b), first fastening device (3), second fastening device (6), flap (5), and fold line (11). The distance between the edge of the bag (9) and the depth of the notch (11) in second side wall (2b) are dimensions which are set forth hereinabove.

FIG. 6 depicts an un-notched venting bag with the article (1) loosely contained therein.

The Bag Dimensions given hereinabove are for containment bags which are designed to tumble freely within the drum of a conventional, U.S.-style in-home hot air clothes dryer having a drum volume of about 170–210 liters (home size). The bag of the stated dimensions is designed to treat up to about 5 kg fabric load in a single use. The dimensions can be adjusted proportionately for larger or smaller bags to achieve the desired VVE and to ensure effective use in dryers with larger or smaller drums. For example, the total volume of a containment bag constructed for use in an average European home clothes dryer (or U.S. "apartment" size; ca. 90 liter drum volume) would be about 60% of the volume for an average U.S. dryer.

OVERALL PROCESS

The overall process is conveniently conducted in a tumbling apparatus, preferably in the presence of heat. The nylon or other heat-resistant vapor-venting bag with the article herein plus aqueous cleaning/refreshment composition and containing the fabric being treated is closed and placed in the drum of an automatic hot air clothes dryer at temperatures of from about 40° C. to about 250° C., preferably, from about 40° C. to about 150° C. The drum is allowed to revolve, which imparts a tumbling action to the bag and agitation of its contents concurrently with the tumbling. By virtue of this agitation, the fabrics come in contact with the article containing the composition. The tumbling and heating are carried out for a period of at least about 10 minutes, typically from about 20 minutes to about 60 minutes. This step can be conducted for longer or shorter periods, depending on such factors as the degree and type of soiling of the fabrics, the nature of the soils, the nature of the fabrics, the fabric load, the amount of heat applied, and the like, according to the needs of the user. During the step, greater than about 40%, typically 40% to about 80%, of the moisture is vented from the bag.

The following Examples further illustrate the invention, but are not intended to be limiting thereof.

EXAMPLE I

A low residue liquid fabric cleaning/refreshment product for use in a vented dryer bag is prepared, as follows.

| Ingredient | % (wt.) |
|---|---|
| Antimicrobial Agent | 0.5 |
| Emulsifier (TWEEN 20)* | 0.5 |
| Perfume | 0.5 |
| KATHON ® | 0.0003 |
| Sodium Benzoate | 0.1 |
| Water | Balance |

*Polyoxyethylene (20) sorbitan monolaurate available from ICI Surfactants.

A 10¼ in.×14¼ in. (26 cm×36 cm) carrier sheet of HYDRASPUN® is prepared. The carrier sheet is covered on both sides with a topsheet and a bottomsheet of 8 mil (0.2 mm) Reemay fabric coversheet material of the type described hereinabove. The coversheet (i.e., both topsheet and bottomsheet) are bonded to the carrier sheet by a Vertrod® or other standard heat sealer device, thereby bonding the laminate structure together around the entire periphery of the carrier sheet. The edges of the carrier sheet around its periphery are intercalated between the topsheet and bottomsheet by the bond. As noted above, the width of the bond is kept to a minimum and is about 0.25 in. (6.4 mm).

The bonded laminate structure thus prepared is folded and placed in a pouch. Any plastic pouch which does not leak would be suitable. For example, a foil laminated pouch of the type used in the food service industry can be employed. Such pouches are well-known in the industry and are made from materials which do not absorb food flavors. In like manner, the formulator herein may wish to avoid absorption of the perfume used in the cleaning/refreshment composition by the pouch. Various pouches are useful herein and are commercially available on a routine basis.

The folded carrier sheet/coversheet article is placed in the pouch. The folds can be of any type, e.g., an accordion-style fold, such that the final dimension of the folded sheet is about 13.5 cm×9.5 cm. This size is not critical but is convenient for placement in a pouch. 23 Grams of the liquid product are poured onto the carrier sheet/coversheet and allowed to absorb into it for a minimum of 30 minutes, preferably for about 4 hours. The pouch is sealed immediately after the liquid product is introduced into the pouch and stored until time-of-use.

In an alternate mode, the article can be rolled somewhat loosely around a cylindrical void into a generally tubular shape of about 26 cm length and a diameter of about 2–3 cm. The rolled article is then folded to half its length at about its mid-point by means of a thrusting blade which also serves to insert the article into a retaining pouch. It is observed that, with such rolling method, essentially no severely sharp creases are formed, and the final doubling of the rolled tube is under such stress that only in the very center of the bend are a few sharper creases formed. The result is that permanent refolding along crease lines is essentially avoided, and release of the cleaning/refreshment composition from the article in-use is optimized.

Any plastic or flexible pouch which does not leak is suitable for use herein. For example, a foil laminated pouch of the type used in the food service industry can be employed. Such pouches are well-known in the industry and are made from materials which do not absorb food flavors. In like manner, the formulator herein may wish to avoid absorption of the perfume used in the cleaning/refreshment composition by the pouch. Various pouches are useful herein and are commercially available on a routine basis. As a point of comparison, the pouch containing the rolled/folded article herein has overall dimensions of about 8.5 cm×17.7 cm, whereas a pouch for a similar planar-folded article is about 13 cm×17.7 cm.

As an entirely optional matter, the carrier sheet can also have holes punched therethrough in order to further maximize its ability to maintain an open configuration in-use. Indeed, the holes can be punched through the entire article, including the coversheet, itself. For an article having the overall dimensions of about 27 cm×37 cm, 16 round holes, each about 0.5 in. (1.27 cm) in diameter are evenly spaced across the HYDRASPUN carrier sheet. Slits or other perforations may be used in like manner.

The fabric to be treated is placed into a 26 in.×30 in. (66×76 cm) vapor-venting nylon bag as shown in the Figures together with the sheet (which is removed from its storage pouch, unfolded and/or unrolled) releasably containing the aforesaid cleaning/refreshment product. The mouth of the bag is closed to provide vapor-venting, and the bag and its contents are placed in the drum of a conventional hot air clothes dryer. The dryer is operated in standard fashion for 20–60 minutes at a high heat setting (an air temperature range of about 140–170° F.; 60–70° C.). After the tumbling action of the dryer ceases, the cleaned and refreshed fabric is removed from the bag. The used sheet is discarded. The fabric (which is preferably still slightly damp) is preferably hung on a conventional hanger to complete the drying process thereby further avoiding wrinkles.

EXAMPLE II

Aspergillus niger is selected as a typical fungal microorganism, that is, as a test microbial. Fabrics inoculated therewith are treated in the manner of this invention using the vented bag. As a control, fabrics are similarly inoculated with the test microbials and are left unexposed to the dryer treatment. The results indicate that at least about 90% of the test microbes initially present were killed by the test treatment. These results would not be expected by those skilled in the art.

EXAMPLE III

Escherichia coli is selected as a typical bacterial microorganism, that is, as a test microbial. Fabrics inoculated therewith are treated in the manner of this invention using the vented bag. As a control, fabrics are similarly inoculated with the test microbials and are left unexposed to the dryer treatment. The results indicate that greater than 99.97% of the test microbes initially present were killed by the test treatment. These results would not be expected by those skilled in the art.

What is claimed is:

1. A process for sanitizing a fabric article which is contaminated with one or more microbials, the process comprising the steps of:
   a) placing the fabric article in a vapor venting bag together with a cleaning/refreshing composition comprising water and at least one antimicrobial agent selected from the group consisting of 5-chloro-2-(2,4-dichlorophenoxy)phenol, trichlorocarbanalide, 4-chloro-3,5-dimethylphenol, iodine/iodophors, chlorhexidine, phenols, phospholipids, thymol, eugeniol, geraniol, oil of lemon grass, limonene and mixtures thereof;
   b) subjecting the vapor venting bag to a heat source which supplies sufficient heat to vaporize the water, thereby exposing the microbials to the resulting water vapor and the antimicrobial agent; and
   whereby at least about 50% of the microbes are killed.

2. A process according to claim 1, wherein the cleaning/refreshing composition comprises a second antimicrobial agent selected from the group consisting of alkyl alkoxy sulfates, linear alkyl benzene sulfonates, aminc oxides, polyhydroxy fatty acid amides, ethoxylated alcohols, diamines, amides, alkyl polyglucosides, betaines, and mixtures thereof.

3. A process according to claim 1, wherein the cleaning/refreshing composition comprises a nonionic surfactant.

4. A process according to claim 1, wherein the cleaning/refreshing composition comprises a perfume.

5. A process according to claim 1, wherein the cleaning/refreshing composition is releasably absorbed in a carrier.

6. A process according to claim 5, wherein the carrier is in sheet form.

7. A process according to claim 6, wherein the carrier comprises a fibrous, hydroentangled web.

8. A process according to claim 1, which additionally comprises the step of subjecting the vapor venting bag to a tumbling action concurrently with the heat source.

9. A process according to claim 8, wherein the heat source and tumbling action are supplied by a hot air clothes dryer.

10. A process according to claim 1, wherein the vapor venting bag has a VVE rating of at least about 40.

11. A process according to claim 10, wherein the vapor venting bag has a VVE rating of at least about 60.

12. A process according to claim 10, wherein the vapor venting bag has a VVE no greater than about 90.

13. A process according to claim 10, wherein the vapor venting bag has a VVE no greater than about 80.

14. A process according to claim 1, further comprising the step of pre-treating at least a portion of the fabric with a pre-treating composition comprising an antimicrobial agent selected from the group consisting of hydrogen peroxide, other oxygen bleaches, 5-chloro-2-(2,4-dichlorophenoxy) phenol, trichlorcarbanilide, hexachlorophene, chlorhexadine, o-phenylphenol, benzylquaternium salts and mixtures thereof.

15. A process according to claim 14, wherein the pre-treating composition comprises from about 0.05% to about 3%, by weight of the antimicrobial agent.

16. A process according to claim 1, wherein the cleaning/refreshing composition comprises from about 0.05% to about 3%, by weight of the antimicrobial agent.

17. A process according to 1, wherein the microbials are selected from group consisting of germs, bacteria, viruses, parasites, fungi/spores and mixtures thereof.

18. A process according to claim 17, wherein the microbials are a mixture of fungi.

19. A process according to claim 9, wherein the hot air clothes dryer operates at temperature of from about 40° C. to about 250° C.

20. A process according to claim 1, whereby at least about 90% of the microbes are killed.

* * * * *